United States Patent [19]

Lavash

[11] Patent Number: 4,523,334
[45] Date of Patent: Jun. 18, 1985

[54] DISPOSABLE BIB HAVING FIBROUS TOPSHEET WHEREIN MOTHER'S-BOND ZONE IS IMPREGNATED WITH BONDING MATERIAL

[75] Inventor: Bruce W. Lavash, Cincinnati, Ohio
[73] Assignee: The Procter & Gamble Company, Cincinnati, Ohio
[21] Appl. No.: 549,371
[22] Filed: Nov. 4, 1983
[51] Int. Cl.³ .................. A41B 13/10; A41D 13/04
[52] U.S. Cl. ................................ 2/49 R; 604/390
[58] Field of Search .................... 2/49 R, 50, 51; 604/390, 389, 386

[56] References Cited

U.S. PATENT DOCUMENTS

| | | | |
|---|---|---|---|
| 24,043 | 7/1955 | Barager | 2/49 |
| 2,782,420 | 2/1957 | Barager | 2/49 |
| 3,146,464 | 9/1964 | Burnett | 2/49 |
| 3,328,807 | 7/1967 | Strauss | 2/49 |
| 3,416,157 | 12/1968 | Marder et al. | 2/49 |
| 3,642,001 | 2/1972 | Sabee | 604/390 |
| 3,867,940 | 2/1975 | Mesek et al. | 128/287 |
| 3,901,237 | 8/1975 | Cepuritis et al. | 128/284 |
| 3,995,321 | 12/1976 | Johnson | 2/49 |
| 4,055,183 | 10/1977 | Ryan et al. | 128/287 |
| 4,210,144 | 7/1980 | Sarge et al. | 128/287 |

Primary Examiner—Louis K. Rimrodt
Assistant Examiner—J. L. Kravitz
Attorney, Agent, or Firm—Thomas J. Slone; Fredrick H. Braun; Richard C. Witte

[57] ABSTRACT

A disposable bib having a fibrous topsheet and a tape-tab fastener wherein a predetermined mother's-bond zone of the topsheet is sufficiently impregnated with a bonding material such as a non-pressure sensitive bonding material to enable the mother's-bond end of the tape-tab fastener to be operatively secured to the mother's-bond zone: preferably, refastenably secured thereto so that, for example, an unsoiled bib may be removed for alter use. In a preferred embodiment which comprises a laminate of flexible sheet material, the laminate comprises a tissue paper topsheet having insufficient strength to operatively accept the mother's-bond end of the tape-tab fastener; and a liquid impervious backsheet of, for example, polyethylene film. The topsheet and the backsheet are preferably bonded together as for example with spaced zones of laminating bonding material; and, preferably, the mother's-bond area of the topsheet is sufficiently impregnated with the non-pressure sensitive bonding material that a continuum of bonding material is established from the frontal surface of the topsheet to the frontal surface of the backsheet at least through the spaced zones of laminating bonding material.

3 Claims, 3 Drawing Figures

DISPOSABLE BIB HAVING FIBROUS TOPSHEET WHEREIN MOTHER'S-BOND ZONE IS IMPREGNATED WITH BONDING MATERIAL

DESCRIPTION

1. Technical Field

This invention pertains to disposable garments such as bibs or aprons or the like which are fitted with tape-tab fasteners. More particularly, it pertains to such garments having fibrous topsheets which have insufficient inherent strength to have tape-tab fastener ends operatively secured thereto; and which garments have predetermined zones of their fibrous topsheets sufficiently impregnated with bonding material to enable operative adherence thereto of tape-tab fastener ends.

2. BACKGROUND ART

Disposable bibs having from surface areas coated with adhesives which co-act with like coated area (eg, coated with contact type adhesives) are disclosed in the following U.S. Pat. Nos.: Re. 24,043 which issued July 26, 1955 to E. D. Barager; 2,782,420 which issued Feb. 26, 1957 to E. D. Barager; 3,328,807 which issued July 4, 1967 to K. Strauss; 3,146,464 which issued Sept. 1, 1964 to E. N. Burnett; 3,416,157 which issued Dec. 17, 1968 to H. L. Marder et al; and 3,995,321 which issued Dec. 7, 1976 to Sally Johnson.

Disposable diapers having portions of their impervious backsheets coated with pressure sensitive adhesive presented through cutout regions in their absorbent members are disclosed in U.S. Pat. No. 3,901,237 which issued Aug. 26, 1975 to T. Cepuritis et al.; and U.S. Pat. No. 4,055,183 which issued Oct. 25, 1977 to A. S. Ryan et al discloses another disposable diaper contruction wherein regions of the absorbent filler are cutout to provide a stronger construction for its tape-tab fasteners.

U.S. Pat. No. 3,867,940 which issued Feb. 25, 1975 to Frederick K. Mesek et al discloses a Scrim Reinforced Disposable Diaper wherein scrim is laminated to the backsheet for reinforcement thereof in the tape attachment region and other regions; and U.S. Pat. No. 4,210,144 which issued July 1, 1980 to Henry D. Sarge et al discloses a Disposable Diaper Having Refastenable Tape System wherein the backsheet of the diaper is reinforced by a coating comprising a self-adhering coating material having a relatively high tensile strength and a low elongation to tensile force property relative to the backsheet.

DISCLOSURE OF THE INVENTION

In accordance with one aspect of the present invention, a disposabole bib is provided which comprises a fibrous topsheet, a liquid impervious backsheet, means bonding the topsheet and the backsheet together in laminated relation, a neck-accommodating aperture, a line-of-parting which extends from the edge of the aperture to an adjacent outer edge of the bib, and securement means for bridging the line-of-parting after it has been parted to enable securing the bib on a wearer. The securement means comprises a mother's-bond area of the front surface of the topsheet disposed adjacent the line-of-parting, and a tape-tab fastener disposed and configured to bridge the line-of-parting after it has been manually parted so that a first end (ie, the mother's-bond end) of the tape-tab fastener is secured by pressure sensitive adhesive thereon to the mother's-bond area. The sheet of flexible material from which the bib body per se is made is preferably high bulk, absorbent tissue paper which has an insufficient inherent strength property to enable operative securement thereto of the mother's-bond end of the fastener. Thus, the mother's-bond area or portion of the topsheet is sufficiently impregnated with bonding material to effect sufficient interfiber bonding to enable operative securement thereto of the mother's-bond end of the fastener. Such impregnation may also be effected in the topsheet on the opposite side of the line-of-parting to also enable fastening the factory-bond end of the tape-tab fastener thereto. The impregnation is preferably effected to provide a continuum of the impregnant between the front surface of the topsheet and the front surface of the backsheet; and the continuum may include the laminating bonding medium; eg, laminating adhesive. The impregnating bonding material may, for example, be a non-pressure-sensitive, non-contact type inter-fiber adhesive or bonding material; and may additionally enable refastenable application of the mother's-bond end of the tape-tab fastener or, indeed, both ends of a duplex tape-tab fastener which may have either end unfastened and refastened during use at the user's discretion.

BRIEF DESCRIPTION OF THE DRAWINGS

While the specification concludes with claims which particularly point out and distinctly claim the subject matter regarded as forming the present invention, it is believed the invention will be better understood from the following description taken in conjunction with the accompanying drawings in which:

DETAILED DESCRIPTION OF THE INVENTION

Figure 1:
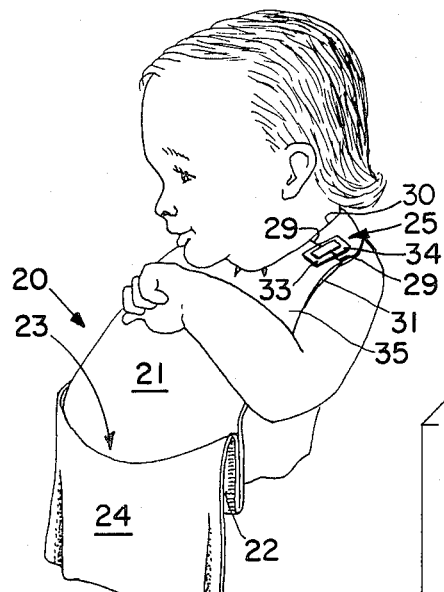
FIG. 1 is a perspective view of a disposable bib embodiment of the present invention which bib is secured on a wearer: an infant.

An exemplary disposable bib 20 embodying the present invention is shown in perspective in FIG. 1 to comprise a body panel 21, a pocket panel 22 which extends the full width of the body panel to form a full-width pocket 23, an apron panel 24 which pendulously depends from the top edge of the pocket panel 22, and a duplex tape-tab fastener 25 which bridges a line-of-severance 29 which extends between the edge 30 of a neck-aperture in the body panel 21 and an adjacent outer edge 31. Additionally, bib 20 is shown to have reinforced areas 33 and 34 disposed adjacent the line-of-severance 29. The reinforced areas 33 and 34 are, nominally, designated the mother's-bond area and the factory-bond area, respectively, of the front surface 35 of body panel 22, and has the tape-tab fastener 25 adhered thereto. The end portions of tape-tab fastener 25 which are secured to areas 33 and 34 are designated 40.

Figure 2:
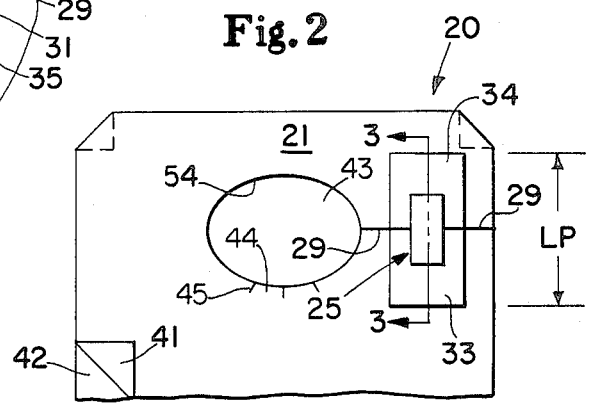
FIG. 2 is an enlarged scale plan view of a fragmentary portion of the bib of FIG. 1 which fragment includes its tape-tab fastener area: the left-shoulder region of the bib.

The left shoulder portion of bib 20, FIG. 1, is shown in enlarged scale in FIG. 2. Body panel 21 is shown to be a laminate comprising a topsheet lamina 41 and a backsheet lamina 42. In an exemplary embodiment of bib 20, lamina 41 comprises a sheet of high bulk, absorbent tissue paper having a basis weight of about twentytwo (22) pounds per three-thousand square feet (about 35.9 grams per square meter) and a nominal caliper of about fourteen (14) mils (about 0.36 mm.); backsheet lamina 42 comprises a polyethylene film having a nominal thickness of about one mil (about 0.0254 mm); and the laminae are preferably secured together with a pattern of discrete areas bonding together with, for example, National Starch Co. adhesive number NS 34-2857. As also indicated in FIG. 2, the neck-accommodating aperture is designated 43 having edge 54; and a portion of the body panel 21 disposed adjacent edge 54 is shown to be subdivided into a plurality of cantilevered petals 44 by cuts 45 which extend radially outwardly from edge 54 to provide comfortable conformance to the user's neck when the bib is applied as shown in FIG. 1.

Figure 3:
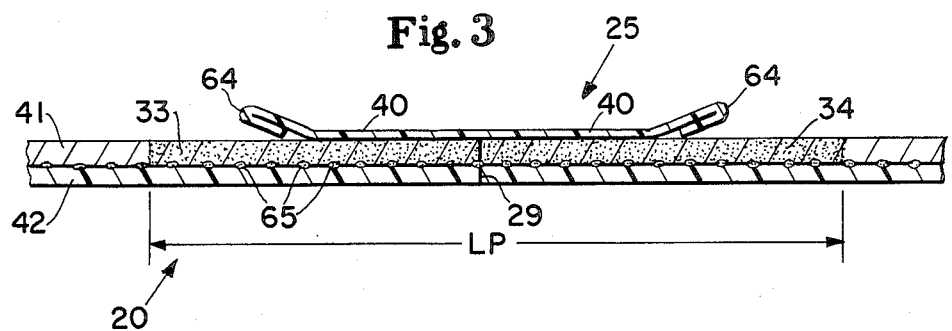
FIG. 3 is a more enlarged scale, sectional view of the bib fragment of FIG. 2 and is taken along line 3—3 of FIG. 2.

FIG. 3 is a fragmentary sectional view along line 3—3 of FIG. 2, and in which the thicknesses of the members have been greatly exaggerated to clearly show their functional features. FIG. 3 shows the left shoulder portion of bib 20 having a duplex tape-tab fastener 25 adhered to the top surface of topsheet 41 superjacent impregnated areas 33 and 34, and in a bridging relation with the line-of-severance 29. As also shown in FIG. 3, the topsheet lamina 41 and the backsheet lamina 42 are secured together with spaced areas of adhesive 65. It is, however, not intended to thereby limit the means for laminating to adhesive per se; nor is it intended to limit the invention to only laminated structures per se. Additionally, it is not intended to limit the invention to bib embodiments having duplex tape-tab fasteners (ie, fasteners having both ends refastenable) nor to embodiments having both tape-ends disposed on front surface areas.

Still referring to FIG. 3, the reinforced zones or areas 33 and 34 of topsheet 41 are impregnated with a bonding material: such as, for example, Petrothene NA 601-00 from U.S.I. Chemicals Company, or Eastobond A-3 from Eastman Adhesive. Such bonding materials are applied to area 33 in sufficient quantity to enable operative attachment of the mother's-bond end 40 of tape-tab 25 thereto. That is, lamina 41 of suitable basis weight and bulk paper have insufficient inherent strength to enable operative attachment thereto of tape-tab end 40 thereto: ie, with sufficient strength to withstand forces imposed by applying the bib to a wearer and during the normal usage of the bib. Therefore, area 33 of lamina 41 is sufficiently impregnated with bonding material to enable the mother's-bond tape joint to withstand the rigors of application and use: ie, operative attachment. Area 34 is similarly impregnated so that it may operatively accept the other end of a duplex tape-tab fastener in the manner shown in the figures; or, for tape-tabs having a permanently adhered factory-bond end, that the factory-bond region of the body panel is sufficiently strong to withstand the rigors of application and use of the bib even though the factory-bond end of fastener 25 is not secured to area 34 per se. Additionally, it is preferable to sufficiently impregnate areas 33 and 34 with bonding material to form a continuum of bonding material from the top surface of lamina 41 to the front surface of lamina 42 so that the strength property of the backsheet lamina 42 is added—at least in part—to the strength of the impregnated areas. The impregnating bonding material may effect such a continuum directly with the front surface of lamina 42, or through the zones 65 of laminating adhesive, or both as indicated in FIG. 3.

While particular embodiments of the present invention have been illustrated and described, it would be obvious to those skilled in the art that various other changes and modifications can be made without departing from the spirit and scope of the invention. It is intended to cover in the appended claims all such changes and modifications that are within the scope of this invention.

What is claimed is:

1. A disposable bib comprising a fibrous topsheet, a liquid impervious backsheet, means bonding said topsheet and said backsheet together in laminated relation, a neck accommodating aperture disposed adjacent one end of said bib, a line-of-parting extending from the edge of said neck accommodating aperture to an adjacent outer edge of said bib, and securement means for bridging said line-of-parting after parting to secure said bib on a wearer for use, said securement means comprising a mother's-bond area of said topsheet disposed adjacent said line-of-parting, and a tape-tab fastener disposed and configured to bridge said line-of-parting when parted with a first end of said tape-tab fastener secured by pressure sensitive adhesive thereon to the front surface of said mother's-bond area, said fibrous topsheet having an insufficient inherent strength property to enable operative association with said first end of said tape-tab fastener, said mother's-bond area being a zone of said topsheet which is sufficiently impregnated with bonding material to provide a tensile-force-transmitting continuum of said bonding material between the front surface of said mother's-bond area of said topsheet and the front surface of underlying portions of said backsheet so that said sheets are united whereby the strength property of said portions of said backsheet lamina is added to the strength of said impregnated zone of said topsheet, and to effect sufficient interfiber bonding in said zone that said zone has sufficient strength to enable said first end of said tape fastener to be and remain operatively secured thereto during normal use of said bib.

2. The disposable bib of claim 1 wherein said bonding material is a non-pressure sensitive inter-fiber adhesive.

3. The disposable bib of claim 2 wherein said tape-tab fastener, said bonding material and said impregnating comprise means for refastenably adhering said first end of said tape-tab fastener to said mother's-bond area of said topsheet.

* * * * *